(12) United States Patent
Chan et al.

(10) Patent No.: US 7,442,720 B2
(45) Date of Patent: *Oct. 28, 2008

(54) COMPOSITIONS AND METHODS FOR TREATING DIABETES

(75) Inventors: Bill Piu Chan, Beijing (CN); Gary Kwan Po Wong, Kowloon (HK); Jinxian Xu, Shanghai (CN); Francis Chi, Kowloon (HK)

(73) Assignee: Omega Bio-Pharma (I.P.3) Limited, Kowloon (HK)

( * ) Notice: Subject to any disclaimer, the term of this patent is extended or adjusted under 35 U.S.C. 154(b) by 321 days.

This patent is subject to a terminal disclaimer.

(21) Appl. No.: 11/017,164

(22) Filed: Dec. 20, 2004

(65) Prior Publication Data

US 2005/0137125 A1   Jun. 23, 2005

Related U.S. Application Data

(60) Provisional application No. 60/591,709, filed on Jul. 27, 2004, provisional application No. 60/531,119, filed on Dec. 19, 2003.

(51) Int. Cl.
*A61K 31/13* (2006.01)
*A61K 31/28* (2006.01)
*A61K 31/155* (2006.01)

(52) U.S. Cl. .................... 514/665; 514/3; 514/635; 514/866

(58) Field of Classification Search .................. 514/23, 514/58, 265, 369, 458, 539, 635, 866
See application file for complete search history.

(56) References Cited

U.S. PATENT DOCUMENTS

| | | | |
|---|---|---|---|
| 5,284,874 A | 2/1994 | Clark et al. |
| 5,401,880 A | 3/1995 | Clark et al. |
| 5,668,117 A | 9/1997 | Shapiro |
| 5,714,519 A | 2/1998 | Cincotta et al. |
| 6,521,266 B1 | 2/2003 | Mann |
| 6,630,176 B2 | 10/2003 | Li et al. |
| 6,746,678 B1 | 6/2004 | Shapiro |
| 2004/0033985 A1 | 2/2004 | Chi et al. |
| 2004/0106591 A1 | 6/2004 | Pacioretty et al. |
| 2005/0143473 A1 | 6/2005 | Wong et al. |

2005/0148674 A1   7/2005 Tang et al.

FOREIGN PATENT DOCUMENTS

| JP | 2002187839 | 7/2002 |
|---|---|---|
| WO | WO 95/01096 A1 | 1/1995 |
| WO | WO 01/95944 A3 | 12/2001 |

OTHER PUBLICATIONS

Http://www.Drugs.com/metformin.html (2007).*
Http://www.people.vcu.edu/urdesai/bigu.htm (2007).*
Http://en.wikipedia.org/wiki/Buformin (2007).*
Kano, M. et al., "Soymilk Products Affect Ethanol Absorption and Metabolism in Rats During Acute and Chronic Ethanol Intake," *American Society for Nutritional Sciences*, 2002, pp. 238-244.
Vescei et al., "Preclinical and Clinical Studies With Cysteamine and Pantethine Related to the Central Nervous System," *Prg. Neuropsychopharmacol.*, 1990, 14:835-862.
Wall, T. L. et al., "Alcohol Metabolism in Asian American Men With Genetic Polymorphisms of Aldehyde Dehydrogenase," *Annals of Int. Med.*, 1997, 127(5):376-379.
Windholz et al., The Merck Index, Tenth Edition, 1983, pp. 849-850, abstract No. 5792.
U.S. Appl. No. 11/118,737, filed Apr. 29, 2005.
Gennes, J.L. et al., "Effets De Cystamine Dans Differentes Affections Allergiques," *Semaine Des Hopitaux De Paris, Expansion Scientifique Francaise* (1956), 32(56): 2850-2853.
Gyenes, L. et al., "The Properties of Fragments of Skin-Sensitizing and Blocking Antibodies as Revealed by the Prausnitz-Kuestner, Passive Cutaneous Anaphylaxis and Hemagglutination Reactions," *International Archives of Allergy and Applied Immunology* (1964), 24: 106-118.
Landers, M. C. et al., "Permanent-Wave Dermatitis: Contact Allergy to Cysteamine Hydrochloride," *American Journal of Contact Dermatitis* (2003), 14(3): 157-160.

* cited by examiner

*Primary Examiner*—Kevin E Weddington
(74) *Attorney, Agent, or Firm*—Saliwanchik, Lloyd & Saliwanchik

(57) ABSTRACT

The subject invention provides compositions and methods for treating diabetes in patients. In a preferred embodiment, the invention provides compositions methods for treating diabetes and/or preventing or alleviating complications associated with diabetes. Specifically exemplified herein is the concurrent administration of a cysteamine compound with at least one additional therapeutic agent to prevent and/or treat diabetes as well as prevent and/or treat complications associated with diabetes. In a preferred embodiment, oral administration of cysteamine hydrochloride with Metformin to a patient diagnosed with diabetes can substantially regulate the patient's glucose metabolism and insulin sensitivity.

5 Claims, 5 Drawing Sheets

COMPOSITIONS AND METHODS FOR TREATING DIABETES

CROSS-REFERENCE TO A RELATED APPLICATION

This application claims the benefit of U.S. provisional application Ser. Nos. 60/531,119, filed Dec. 19, 2003, and 60/591,709, filed Jul. 27, 2004.

BACKGROUND OF THE INVENTION

Diabetes is a chronic disease that has no cure. Currently, about 18.2 million people or 6.3% of the population in the United States have diabetes. While roughly 13 million have been diagnosed, it is estimated that 5.2 million people are not aware that they have the disease. As the $6^{th}$ leading cause of death by disease in 2000, diabetes is costing the US health care system an estimated $132 billion annually. National Diabetes Information Clearinghouse, NIH Publication No. 04-3892, Nov. 2003. More serious than the economic costs associated with diabetes are the decrease in quality of life, serious health complications/consequences, and deaths associated with diabetes.

With about 12,000 to 24,000 new cases each year, diabetes is the leading cause of new cases of blindness in adults ages 20-74. Diabetes is also the leading cause of end-stage renal disease, accounting for about 44% of new cases annually. In 2001 alone, approximately 42,800 people initiated treatment for end stage renal disease (kidney failure) because of diabetes. About 60-70 percent of people with diabetes have mild to severe forms of diabetic nerve damage, which, in severe forms, can lead to lower limb amputations. In fact, more than 60% of non-traumatic, lower limb amputations are performed on persons with diabetes. In 2002-2003, about 82,000 non-traumatic, lower limb amputations were performed on persons with diabetes. People with diabetes are 2 to 4 times more likely to suffer a stroke. Moreover, adults with diabetes have heart disease death rates about 2 to 4 times higher than those without diabetes.

Diabetes is a group of diseases characterized by high blood glucose levels, which result from defects in insulin production, insulin action, or both. Because diabetes can remain undiagnosed for years, many people become aware that they have diabetes only after the development of one of its life-threatening complications. Although the cause of diabetes is still unknown, it is well-accepted that both genetics and environmental factors, such as obesity and lack of exercise, are important factors.

One group of diabetes, Type 1 (or insulin-dependent diabetes mellitus or juvenile-onset diabetes), develops when the body's immune system destroys pancreatic cells that make the hormone insulin, which regulates blood glucose levels. Type 1 diabetes usually occurs in children and young adults; although disease onset can occur at any age. Type 1 diabetes accounts for about 5 to 10 percent of all diagnosed cases of diabetes. Risk factors for Type 1 diabetes include autoimmune, genetic, and environmental factors. Individuals diagnosed with Type 1 diabetes require daily delivery of insulin via injections or pumps.

Another group of diabetes, Type 2 diabetes (or non-insulin-dependent diabetes mellitus or adult-onset diabetes), is a metabolic disorder resulting from the body's inability to make enough, or properly use, insulin. This disease usually begins as insulin resistance, a disorder in which the cells do not use insulin properly, and as the need for insulin rises, the pancreas gradually loses its ability to produce insulin. Type 2 diabetes is the most common form of the disease accounting for 90-95 percent of diabetes. Type 2 diabetes is nearing epidemic proportions, due to an increased number of older Americans, and a greater prevalence of obesity and a sedentary lifestyle.

Gestational diabetes refers to a form of glucose intolerance that is diagnosed in pregnant women. During pregnancy, gestational diabetes requires treatment to normalize maternal blood glucose levels to avoid complications in the infant. A percentage (5-10 percent) of women with gestational diabetes have Type 2 diabetes after pregnancy. Women who have had gestational diabetes also have a 20-50 percent chance of developing diabetes in the next 5-10 years.

Hyperinsulinemia refers to the overproduction of insulin by pancreatic cells. Often, hyperinsulinemia occurs as a result of insulin resistance, which is a condition defined by cellular resistance to the action of insulin. Insulin resistance, as defined above, is a state/disorder in which a normal amount of insulin produces a subnormal biologic (metabolic) response. For example, in insulin-treated patients with diabetes, insulin resistance is considered to be present whenever the therapeutic dose of insulin exceeds the secretory rate of insulin in normal person.

Impaired glucose homeostasis (or metabolism) refers to a condition in which blood sugar levels are higher than normal but not high enough to be classified as diabetes. There are two categories that are considered risk factors for future diabetes and cardiovascular disease. Impaired glucose tolerance (IGT) occurs when the glucose levels following a 2-hour oral glucose tolerance test are between 140 to 199 mg/dl. IGT is a major risk factor for type 2 diabetes and is present in about 11 percent of adults, or approximately 20 million Americans. About 40-45 percent of persons age 65 years or older have either type 2 diabetes or IGT. Impaired fasting glucose (IFG) occurs when the glucose levels following an 8-hour fasting plasma glucose test are greater than 110 but less than 126 mg/dl.

Hyperglycemia, a common feature of diabetes, is caused by decreased glucose utilization by liver and peripheral tissues and an increased glucose production by liver. Glucokinase (GK), the major glucose phosphorylating enzyme in the liver and the pancreatic β-cells, plays an important role in regulating blood glucose homeostasis. Notably, the levels of this enzyme are lowered in patients with type 2 diabetes (Caro, J. F. et al., *Hormone metabolic Res.*, 27;19-22, 1995) and in some diabetic animal models (Barzilai, N. and Rossetti, L. *J. Biol. Chem.*, 268:25019-25025, 1993).

Many pharmaceutical compositions and methods have been proposed to treat and/or cure diabetes. For example, one approach to reducing hyperglycemia in diabetes involves increasing liver GK activity (Van Schaftingen, E. et al., *Adv. Enzyme Regul.* 32:133-148, 1992). Studies involving transgenic diabetic mice have shown that increased GK copy number results in increased hepatic glucose metabolism and decreased plasma glucose levels (Ferre, T. et al., *Proc. Natl. Acad. Sci. USA*, 93:7225-7230 (1996a) and FASEB J, 10:1213-1218, (1996b); Niswender, K. D. et al., *J. Biol. Chem.*, 272:22570-22575 (1997)), demonstrating that increasing liver GK may be effective in reducing hyperglycemia in diabetes. In addition, Hariharan, N. et al. (*Diabetes* 46:11-16 (1997)) have demonstrated that increasing liver GK improves glucose homeostasis and leads to weight reduction in transgenic mice.

Various groups have also demonstrated that glucokinase regulatory protein ("GKRP") binds to GK in the hepatocyte nucleus and may therefore function in vivo to regulate GK activity (Brown, K. S. et al., Diabetes 46:179-186, 1997; De la Iglesia, N. et al., FEBS Left. 456:332-338,1999; Fernandez-Novell, J. M. et al., FEBS Left. 459:211-214, 1999). The relevance of this mechanism in an in vivo setting has been demonstrated in experiments by Cherrington and coworkers (Shiota, M. et al., Diabetes 47:867-873, 1998). In these studies, small amounts of fructose, which is converted to fructose-1-phosphate in the liver and thus should increase free GK, substantially increased net hepatic glucose utilization, analogous to what is seen in the transition from fasted to fed states.

U.S. Pat. No. 5,714,519 (hereinafter the '519 patent) discloses methods for controlling either hyperinsulinemia or insulin resistance by administering panthethine (see claims 1-18; col. 5, lines 6-15) or cysteamine (see claims 19-27; col. 5, lines 16-22) at predetermined intervals during the day. Unfortunately, some of the dosages of panthethine or cysteamine (for example, 500 mg of cysteamine) disclosed in the '519 patent are toxic to humans. In fact, such dosage amounts of cysteamine or panthethine can also cause undesirable gastrointestinal symptoms, such as increased acid output or even ulcers (Srivastava, P. K. & L. Field, "Organic disulfides and related substances. 38. Some disulfide and trisulfide sulfinate salts as antiradiation drugs," *J Med Chem,* 18(8):798-802 (1975)). In addition, the necessary specific times for administration, as taught by the '519 patent, are not conducive to patient compliance with a therapy regimen.

Cysteamine itself is not a very stable chemical compound. Generally, cysteamine very quickly disappears (in minutes) when administered to the body. Therefore, it would be critical to make a stable form of cysteamine, that will be properly metabolized by the body at a target area for optimal therapeutic effect.

The two pharmacological modalities presently used to lower blood sugar are oral hypoglycemic (anti-diabetic) agents and insulin. Insulin replacement is presently accomplished by injection and is based upon the lack of insulin or limitation of its action in diabetes mellitus. Oral anti-diabetic agents are not chemically akin to insulin and their sugar-lowering mechanism differs from the action of direct insulin replacement. Oral hypoglycemic agents and insulin are, at present, therapeutically utilized alone or in concert with each other, according to the needs of the diabetic individual. Some individuals are best treated with more than one oral agent, with, or without insulin For the foregoing reasons, there is a need for new therapeutic treatments for diabetes; particularly for eliminating or reducing symptoms related to diabetes.

BRIEF SUMMARY OF THE INVENTION

The subject invention provides compositions and methods for treating diabetes while ameliorating many unwanted side effects often associated with conventional agents used to treat diabetes. In a preferred embodiment, the invention provides unique compositions and methods for the treatment and/or prevention of diabetes and diabetes related symptoms as well as the prevention or delay in development of diabetes-related complications, conditions or diseases.

The present invention provides compositions comprising a cysteamine compound and at least one additional agent known to be effective in the treatment of diabetes (hereinafter the "additional therapeutic agent"). Specifically exemplified herein is the concurrent administration of a cysteamine compound and at least one additional therapeutic agent to prevent or treat diabetes; and/or reduce or eliminate the severity, intensity, and/or duration of at least one complication associated with diabetes, while ameliorating unwanted side effects often associated with the singular administration of said additional therapeutic agent. The compositions and methods of the invention are particularly efficacious in lowering blood glucose levels.

A therapeutic agent, as defined herein, refers to those agents or therapeutic regimens known to the skilled artisan to be suitable for use in the treatment of diabetes and diabetes-related symptoms. Examples of therapeutic agents include, but are not limited to, gene-based pharmaceutical compounds; insulin; sulfonylureas (i.e., glyburide, glipizide, glimepiride, tolbutamide, chlorpropramide); insulin secretagogues (i.e., repaglinide, nateglinide); α-glucosidase inhibitors (i.e., acarbose, miglitol); biguanides (i.e., Metformin); and thiazolidinediones (i.e., rosiglitazone, piaglitazone). meglitinides, and D-phenylalanine. These available therapeutic agents, which have not changed substantially in many years, have recognized limitations when administered alone (e.g., without the concurrent administration of a cysteamine compound).

In a method of use, a cysteamine compound is concurrently administered with at least one additional therapeutic agent to a patient prior to or after diagnosis with diabetes to treat diabetes and diabetes related symptoms. In a related embodiment, a cysteamine compound is administered concurrently with at least one additional therapeutic agent selected from the group consisting of gene-based pharmaceutical compounds, insulin, sulfonylureas, biguanides, α-glucosidase inhibitors, thiazolidinediones, meglitinides, and D-phenylalanine to either prevent and/or treat diabetes and diabetes-related complications. Additional contemplated additional therapeutic agents that can be used in accordance with the subject invention to prevent the onset of diabetes include, but are not limited to the following regimens: physical exercise (i.e., moderate physical activity for at least half an hour per day), improved dietary intake (i.e., decrease intake of sugars), and reduction in weight. According to the subject invention, the compositions of the invention can be administered at any time (such as at an undetermined time) to elicit a therapeutic effect.

The following are unwanted side effects often associated with the administration of conventional therapeutic agents: (1) increase in insulin concentrations high enough to stimulate insulin-resistant tissues as a result of increasing the plasma level of insulin by the administration of sulfonylureas (i.e., tolbutamide and glipizide) or meglitinide, which stimulate the pancreatic β-cells to secrete more insulin, and/or by injection of insulin when sulfonylureas or meglitinide become ineffective; (2) dangerously low levels of plasma glucose can result from administration of insulin or insulin secretagogues (sulfonylureas or meglitinide), and an increased level of insulin resistance due to the even higher plasma insulin levels can occur; (3) inability to be combined with other therapies used to treat diabetes (i.e., clinical caution when combining sulfonylureas drugs with other diabetic drugs); and (4) physical discomfort (i.e., increased body weight, increased fluid retention, increased low density lipoprotein levels, flatulence, and diarrhea).

According to the present invention, for the first time it has been discovered that the administration of a cysteamine compound to a patient can increase glucose transporter expression and adiponectin levels. Both increased glucose transporter expression and adiponectin levels can improve patient insulin sensitivity and thus enable the cysteamine compound and additional therapeutic agent(s) to act in a highly beneficial fashion to ensure enhanced therapeutic effect, which would not be observed with the singular administration of either the cysteamine compound or the additional therapeutic agent alone.

Also in accordance with the subject application, the administration of a cysteamine compound to a patient has been observed to affect other biological factors that may represent or develop into diabetes-related complications or conditions. For example, according to the present invention, it has been discovered that that administration of a cysteamine compound to a patient can affect the levels of C-peptide, insulin-like growth factors, blood uric acid, free fatty acid, adiponectine, triglyceride, high density lipoprotein (HDL), low density lipoprotein (LDL), and microalbuminuria in a patient. In particular, administration of a cysteamine compound to a patient can: decrease insulin-like growth factor 1 (IGF-1), decrease C-peptide levels, decrease free fatty acid levels, decrease blood uric acid levels, increase adiponetine levels, decrease triglyceride levels, decrease LDL levels, increase HDL levels, and decrease microalbuminuria levels. Because all of these biological factors are relevant to the diagnosis and/or development of diabetes related complications or conditions (see Reist, G C et al., "Changes in IGF activities in human diabetic vitreous," Diabetes, 53(9):2428-35 (Sept. 2004); Janssen J A and Lamberts, S W, "The role of IGF-I in the development of cardiovascular disease in type 2 diabetes mellitus: is prevention possible?" Eur J Endocrinol., 146(4): 467-77 (2002); Chakrabarti, S et al., "C-peptide and retinal microangiopathy in diabetes," Exp Diabesity Res., 5(1):91-6 (Jan.-Mar. 2004); Gottsater, A. et al., "Plasma adiponectin and serum advanced glycated end-products increase and plasma lipid concentrations decrease with increasing duration of type 2 diabetes," Eur J Endocrinol., 151(3):361-6 (September 2004); Tseng, C H., "Independent association of uric acid levels with peripheral arterial disease in Taiwanese patients with Type 2 diabetes," Diabet Med., 21(7):724-9 (Jul. 2004); Liese, A D et al., "Microalbuminuria, central adiposity and hypertension in the non-diabetic urban population of the MONICA Augsburg survey 1994/95," J Hum Hypertens., 15(11):799-804 (2001); and Wollesen, F. et al., "Peripheral atherosclerosis and serum lipoprotein(a) in diabetes," Diabetes Care., 22(1):93-8 (1999)), administration of a cysteamine compound, either alone or concurrently with an additional therapeutic compound, can be used as described to treat diabetes related complications and conditions.

When a cysteamine compound is administered concurrently with at least one additional therapeutic agent, the materials together provide a more advantageous therapeutic effect than any single form delivered alone. Biguanides are generally used to treat non-insulin-dependent diabetes mellitus or type 2 diabetes. The inventors have surprisingly discovered that the combination of a biguanide, such as Metformin, and a cysteamine compound results in better glycemic control than can be achieved using either a biguanide or a cysteamine compound alone. This beneficial effect is particularly effective in patients diagnosed with diabetes mellitus, genetic diabetes, types 1 and 2 diabetes, and gestational diabetes.

In another embodiment, compositions comprising a cysteamine compound and at least one additional therapeutic agent are provided. In a related embodiment, such compositions can also include "inclusion compound host materials" that fix gases, liquids or compounds as inclusion complexes so that the complex may be handled in solid form and the included constituent (such as a cysteamine compound) can be subsequently released (i.e., by exposure to an alkaline environment, by the action of a solvent or by melting).

In yet another embodiment, the subject invention provides compositions and methods for reducing and/or eliminating the severity, intensity, and/or duration of at least one complication associated with diabetes. Complications, conditions and diseases such as background diabetic retinopathy, macular edema, cataracts, necrobiosis lipoidica, diabetic dermopathy, fungal infections, congestive heart failure, kidney disease, diabetic neuropathy, which are commonly associated with diabetes, can be reduced and/or eliminated through the administration, according to the subject invention, of a cysteamine compound and at least one additional therapeutic agent.

Further advantages of the subject invention include prevention of the development of diabetes. In accordance with the subject invention, concurrent administration of a cysteamine compound with at least one additional therapeutic agent to a patient prior to or at the onset of diabetes diagnosis can alter the patient's metabolism so that diabetes does not develop, or develops to a lesser extent than would be observed in the absence of the cysteamine compound and additional therapeutic agent(s). By enhancing insulin sensitivity (i.e., via increased glucose transporter expression), the compositions and methods of the invention may treat and/or prevent diabetes and diabetes-associated symptoms as well as treat and/or prevent diabetes-related complications or conditions. According to the present invention, subjects with abnormal glucose metabolism or insulin resistance, but not full-blown diabetes (e.g. in obesity), should not develop diabetes due to improved glucose utilization and insulin resistance as a result of cysteamine activity (i.e., observed cysteamine modulation of glucose transporters and adiponectin and lipid metabolism).

In accordance with the subject invention, the daily dosage amount of a cysteamine compound administered to a patient diagnosed with diabetes or suffering from complications, conditions, or diseases associated with diabetes is about 0.1 mg to about 400 mg/kg of patient body weight (BW) of cysteamine (or 600 mg/kg of BW cysteamine hydrochloride) or an equivalent molar quantity of a cysteamine compound. Preferably, a daily dose of about 30 mg/kg of BW of cysteamine, or an equivalent molar quantity of a cysteamine compound, is administered to a patient in accordance with the present invention. The dosage amount of the additional therapeutic agent is based on the amount that will elicit a desired response when administered concurrently with a cysteamine compound.

DETAILED DISCLOSURE OF THE INVENTION

Figure 1:
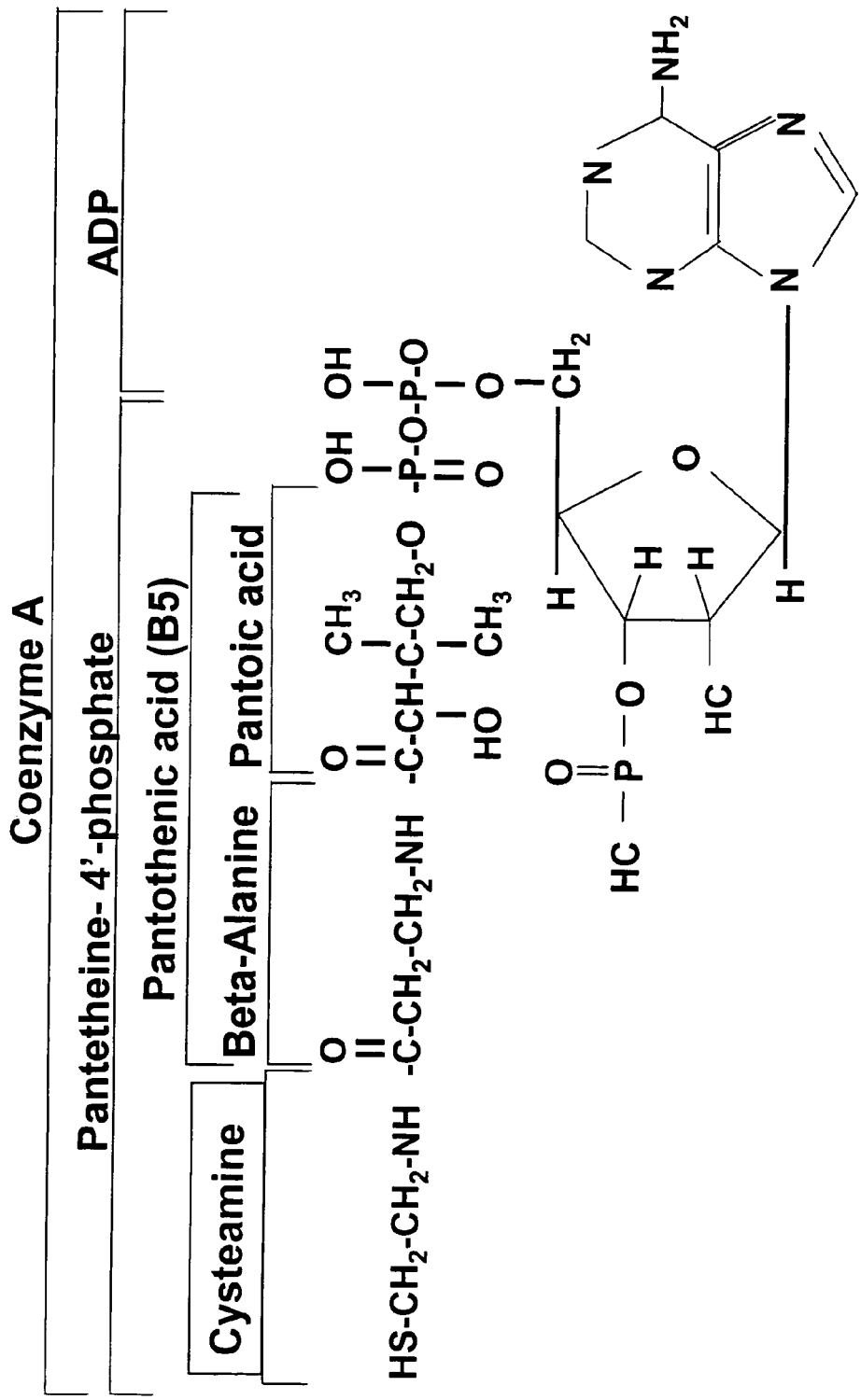
FIG. 1 shows a metabolic pathway of cysteamine.

The subject invention provides methods for treating patients diagnosed with diabetes. The present invention provides, for the first time, beneficial therapeutic combinations of a cysteamine compound and at least one additional therapeutic agent to treat diabetes. In preferred embodiments, the invention provides compositions and methods for treating and/or preventing the development of diabetes as well as the complications associated with diabetes via the concurrent administration of a cysteamine compound and Metformin.

As used herein, the term "diabetes" is intended to mean all diabetic conditions, including, without limitation, diabetes mellitus, genetic diabetes, type 1 diabetes, type 2 diabetes, and gestational diabetes. The term "diabetes" also refers to the chronic disease characterized by relative or absolute deficiency of insulin that results in glucose intolerance. Type 1 diabetes is also referred to as insulin dependent diabetes mellitus (IDDM) and also includes, for example, juvenile-onset diabetes mellitus. Type 1 is primarily due to the destruction of pancreatic β-cells. Type 2 diabetes mellitus is also known as non-insulin dependent diabetes mellitus (NIDDM) and is characterized, in part, by impaired insulin release following a meal. Insulin resistance can also be a factor leading to the occurrence of type 2 diabetes mellitus. Genetic diabetes is due to mutations which interfere with the function and regulation of β-cells.

Diabetes, as used herein, is characterized as a fasting level of blood glucose greater than or equal to about 130 mg/dl or as a plasma glucose level greater than or equal to about 180 mg/dl as assessed at about 2 hours following the oral administration of a glucose load of about 75 g or following a meal. As understood by the skilled artisan, characteristics used in identifying diabetes are subject to change and the latest standards, such as those disclosed by the World Health Organization, can be used to define diabetes as provided in the present invention.

The term "diabetes" is also intended to include those individuals with hyperglycemia, including chronic hyperglycemia, hyperinsulinemia, impaired glucose homeostasis or tolerance, and insulin resistance. Plasma glucose levels in hyperglycemic individuals include, for example, glucose concentrations greater than normal as determined by reliable diagnostic indicators. Such hyperglycemic individuals are at risk or predisposed to developing overt clinical symptoms of diabetes mellitus.

As used herein, the term "diabetic complications" refers to medical/clinical problems that occur more often in patients diagnosed with diabetes. As contemplated herein, diabetic complications include medical/clinical problems that stem from changes in blood vessels and/or nerves as a result of diabetes. These include, and are not limited to, skin conditions (i.e., bacterial infections, fungal infections, diabetic dermopathy, necrobiosis lipoidica, diabeticorum (i.e., bullosis diabeticorum), eruptive xanthomatosis, allergic skin reactions, digital scleroris, disseminated granuloma annulare, and acanthosis nigricans), gum disease, eye disorders (i.e., glaucoma, cataracts, retinopathy, kidney disease, neuropathy (i.e., systemic neuropathy, distal systemic polyneuropathy, proximal neuropathy, femoral neuropathy, neuropathic antrhropathy, cranial neuropathy, authonomic neuropathy, compression neuropathy, and diabetic amyotrophy), gout, and cardiovascular diseases/disorders (i.e., hypertension, heart disease, heart attack, stroke).

The term "patient," as used herein, describes an organism, including mammals, to which treatment with the compositions according to the present invention is provided. Mammalian species that benefit from the disclosed methods of treatment include, and are not limited to, apes, chimpanzees, orangutans, humans, monkeys; and domesticated animals (i.e., pets) such as dogs, cats, mice, rats, guinea pigs, and hamsters.

"Concurrent administration" and "concurrently administering," as used herein, refers to administering at least one additional therapeutic agent suitable for use in the treatment of diabetes (i.e., insulin and/or a hypoglycemic compound). For example, at least one additional therapeutic agent can be provided in admixture with a cysteamine compound, such as in a pharmaceutical composition; or the additional therapeutic agent(s) and cysteamine can be provided as separate compounds, such as, for example, separate pharmaceutical compositions administered consecutively, simultaneously, or at different times. Preferably, if the cysteamine compound and the additional therapeutic agent for treating diabetes are administered separately, they are not administered so distant in time from each other that the cysteamine compound and the additional therapeutic agent cannot interact.

As used herein, reference to a "cysteamine compound" includes cysteamine, the various cysteamine salts (such as cysteamine hydrochloride and cysteamine phosphate) as well as prodrugs of cysteamine that can, for example, be readily metabolized in the body to produce cysteamine. Also included within the scope of the subject invention are analogs, derivatives, conjugates, and metabolites of cysteamine (such as cystamine), which have the ability as, described herein to treat and/or ameliorate complications associated with diabetes. Various analogs, derivatives, conjugates, and metabolites of cysteamine are well known and readily used by those skilled in the art and include, for example, compounds, compositions and methods of delivery as set forth in U.S. Pat. Nos. 6,521,266; 6,468,522; and 5,714,519.

As contemplated herein, a cysteamine compound includes pantothenic acid. Pantothenic acid is a naturally occurring vitamin that is converted in mammals to coenzyme A, a substance vital to many physiological reactions. Cysteamine is a component of coenzyme A, and increasing coenzyme A levels results in increased levels of circulating cysteamine. Alkali metal salts, such as magnesium phosphate tribasic and magnesium sulphite (Epsom salts), enhance formation of coenzyme A. Furthermore, breakdown of coenzyme A to cysteamine is enhanced by the presence of a reducing agent, such as citric acid. Thus, the combination of pantothenic acid and alkali metal salts results in increased coenzyme A production and, concomitantly, cysteamine.

Figure 2:
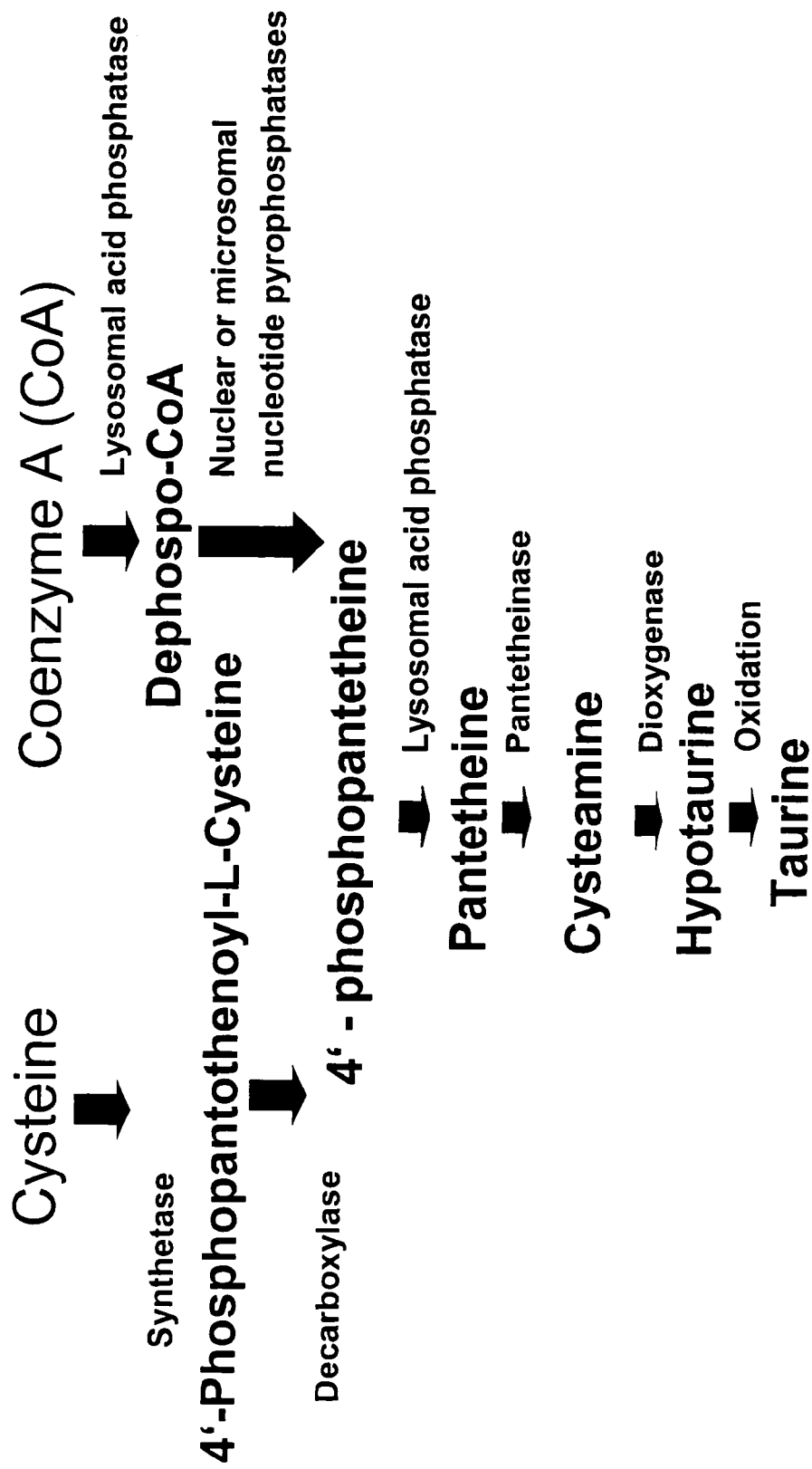
FIG. 2 shows cysteamine as a constituent of co-enzyme A.

Accordingly, in one embodiment of the subject invention, the advantages of concurrently administering a cysteamine compound and at least one additional therapeutic agent, as set forth herein, can be achieved by promoting the endogenous production of cysteamine through natural metabolic process such as through the action of co-enzyme A or as a metabolite of cysteine (see FIGS. 1 and 2). This can be achieved by, for example, the concurrent administration of pantothenic acid and at least one additional therapeutic agent.

The term "effective amount" or "therapeutic effective amount," as used herein, refers to the amount necessary to elicit the desired biological response. In accordance with the subject invention, the therapeutic effective amount is the amount of a cysteamine compound and at least one additional therapeutic agent necessary to treat and/or ameliorate diabetes as well as decrease the severity or prevent a particular diabetes-related complication (i.e., retinopathy, glaucoma, cataracts, heart disease, stroke, hypertension, neuropathy, dermopathy, gum disease, etc.). The decrease maybe a 10%, 20%, 30%, 40%, 50%, 60%, 70%, 80%, 90%, 95%, 98% or 99% decrease in severity of complications.

The present invention provides, for the first time, beneficial therapeutic combinations of a cysteamine compound and at least one additional therapeutic agent to treat diabetes. When a cysteamine compound is administered concurrently with at least one additional therapeutic agent, the materials function advantageously to provide a greater therapeutic effect than any single form delivered alone. Compositions of the present invention, which comprise a cysteamine compound and at least one additional therapeutic agent, are particularly advantageous in treating diabetes and diabetes-related complications since such compositions can be administered at any time (without the need for administration at predetermined time periods) to elicit therapeutic results (i.e., reduction in glucose levels).

Biguanides are generally used to treat non-insulin-dependent diabtetes mellitus. The inventors have surprisingly discovered that the combination of a biguanide (such as Metformin) and a cysteamine compound result in better glycemic control that can be achieved using either an additional therapeutic agent, such as Metformin, and a cysteamine compound alone. This beneficial effect is particularly effective in patients diagnosed with diabetes mellitus, genetic diabetes, types 1 and 2 diabetes, and gestational diabetes.

Specifically exemplified herein is the concurrent administration of cysteamine hydrochloride (and/or analogs, derivatives and prodrugs thereof) and at least one additional therapeutic agent to treat and/or prevent the onset of diabetes in a patient; or to reduce the severity, intensity, or duration of subsequently developed complications related to diabetes. Preferably, the concurrent administration of cysteamine hydrochloride and at least one additional therapeutic agent can be performed at undetermined times. Complications associated with diabetes such as, and not limited to, retinopathy, glaucoma, cataracts, heart disease, hypertension, stroke, gum disease, and dermopathy, can be treated, prevented, and/ or reduced through consumption, according to the subject invention, of a cysteamine compound and at least one additional therapeutic agent.

Further advantages of the subject invention include treatment and/or prevention of the development of diabetes. Specifically, cysteamine (and/or analogs, derivatives, and prodrugs thereof) can be concurrently administered with at least one additional therapeutic agent prior to or upon the diagnosis of diabetes. Alternatively, a cysteamine compound and additional therapeutic agent(s) can be administered concurrently with other known therapies used to treat diabetes.

The additional therapeutic agent, as referred to herein, with which a cysteamine compound is concurrently administered include, without limitation, gene-based pharmaceutical compounds; insulin; sulfonylureas (i.e., glyburide, glipizide, glimepiride, tolbutamide, chlorpropramide); insulin secretagogues (i.e., repaglinide, nateglinide); α-glucosidase inhibitors (i.e., acarbose, miglitol); biguanides (i.e., Metformin); and thiazolidinediones (i.e., rosiglitazone, piaglitazone). meglitinides, D-phenylalanine, physical exercise, improved dietary intake, and reduction in weight.

In one embodiment, a cysteamine compound is administered concurrently with insulin to treat type 1 diabetes, type 2 diabetes, and related conditions and symptoms. For type 2 diabetes, insulin resistance, hyperinsulinemia, diabetes-induced hypertension, obesity, or damage to blood vessels, eyes, kidneys, nerves, autonomic nervous system, skin, connective tissue, or immune system, a cysteamine compound is administered concurrently with a hypoglycemic compound instead of insulin.

Alternatively, a cysteamine compound is administered concurrently with insulin and a hypoglycemic compound to treat type 2 diabetes, insulin resistance, hyperinsulinemia, diabetes-induced hypertension, obesity, or damage to blood vessels, eyes, kidneys, nerves, autonomic nervous system, skin, connective tissue, or immune system.

The compositions of the invention can be used in a variety of routes of administration, including, for example, orally-administrable forms such as tablets, capsules or the like, or via parenteral, intravenous, intramuscular, transdermal, buccal, subcutaneous, suppository, or other route. Such compositions are referred to herein generically as "pharmaceutical compositions." Typically, they can be in unit dosage form, namely, in physically discrete units suitable as unitary dosages for human consumption, each unit containing a predetermined quantity of active ingredient calculated to produce the desired therapeutic effect in association with one or more pharmaceutically acceptable other ingredients, i.e., diluent or carrier.

The cysteamine compounds and additional therapeutic agent(s) of the subject invention can be formulated according to known methods for preparing pharmaceutically useful compositions. Formulations are described in a number of sources, which are well known and readily available to those skilled in the art. For example, *Remington's Pharmaceutical Science* (Martin E W [1995] Easton Pa., Mack Publishing Company, $19^{th}$ ed.) describes formulations that can be used in connection with the subject invention. Formulations suitable for parenteral administration include, for example, aqueous sterile injection solutions, which may contain antioxidants, buffers, bacteriostats, and solutes, which render the formulation isotonic with the blood of the intended recipient; and aqueous and nonaqueous sterile suspensions, which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question.

Concurrent administration of a cysteamine compound and at least one additional therapeutic agent, in accordance with the subject invention, can be accomplished by any suitable method and technique presently or prospectively known to those skilled in the art. In a preferred embodiment, the cysteamine compound and at least one additional therapeutic agent is formulated in a patentable and easily consumed oral formulation such as a pill, lozenge, tablet, gum, beverage, etc. The consumption is then taken at, prior to, or after, the diagnosis of diabetes.

In certain embodiments of the invention, a patient is assessed to identify the risk of developing insulin dependent diabetes mellitus (IDDM) prior to the concurrent administration of a cysteamine compound and at least one additional therapeutic agent (i.e., physical exercise, improved dietary intake, and reduction in weight). Various markers have recently been identified as important markers that predate the clinical onset of IDDM. Immunological markers that can be detected using methods known to the skilled artisan to assess diabetes susceptibility in asymptomatic patients include, but are not limited to, autoantibodies to insulin (IAA); glutamic acid decarboxylase (GAD); and autoantibodies to islet cells (ICA), such as an islet cell member of the receptor type of the tyrosine phosphate family termed IA-2. Methods for identifying asymptomatic patients susceptible to diabetes by detecting such markers, which can be used in accordance with the subject invention, include, but are not limited to, U.S. Pat. Nos. 6,391,651 and 6,316,209.

In accordance with the invention, compositions comprising, as active ingredients, an effective amount of the cysteamine compound and at least one additional therapeutic agent, also include one or more non-toxic, pharmaceutically acceptable carrier or diluent. Examples of such carriers for use in the invention include ethanol, dimethyl sulfoxide, glycerol, silica, alumina, starch, sorbitol, inosital, xylitol, D-xylose, manniol, powdered cellulose, microcrystalline cellulose, talc, colloidal silicon dioxide, calcium carbonate, magnesium cabonate, calcium phosphate, calcium aluminium silicate, aluminium hydroxide, sodium starch phosphate, lecithin, and equivalent carriers and diluents.

In one embodiment, compositions comprising a cysteamine compound, at least one additional therapeutic agent, and a carrier such as inclusion compound host materials are provided. It is believed that by providing a carrier such as inclusion compound host materials, a stabilized cysteamine compound molecule can be safely delivered to a patient at a dosage that will not induce toxicity. In addition, such carrier materials can include coating materials (i.e., enteric-coatings) that allow dissolution of the coating in an alkaline environment such as in the intestines.

An inclusion compound host material that can be used in accordance with the subject invention include those disclosed in U.S. patent application Ser.No. 20040033985, incorporated herein in its entirety. Contemplated inclusion compound host materials include proteins (such as albumin), crown ethers, polyoxyalkylenes, polysiloxanes, zeolites, cholestyramine, colestipol, colesevelam, colestimide, sevelamer, cellulose derivatives, dextran derivatives, starch, starch derivatives, and pharmaceutically acceptable salts thereof. Contemplated cellulose derivatives and dextran derivatives include DEAE-cellulose, guanidinoethylcellulose, or DEAE-Sephadex. Favorable starches or starch derivatives to be included in the compositions of the invention include cyclodextrin, retrograded starch, degraded starch, a combination of retrograded and degraded starch, hydrophobic starch, amylase, starch-diethylaminoethylether, and starch-2-hydroxyethylether.

According to the subject invention, preferred inclusion compound host materials include, but are not limited to, cyclodextrin and/or its derivatives (i.e., methyl β-cyclodextrin (M-β-CD), hydropropyl β-cyclodextrin (HP-β-CD), hydroethyl β-cyclodextrin (HE-β-CD), polycyclodextrin, ethyl β-cyclodextrin (E-β-CD) and branched cyclodextrin. As one skilled in the art will appreciate, any cyclodextrin or mixture of cyclodextrins, cyclodextrin polymers, or modified cyclodextrins can be utilized pursuant to the present invention. Cyclodextrins are available from Wacker Biochem Inc., Adrian, Mich. or Cerestar USA, Hammond, Ind., as well as other vendors. Formation of inclusion complexes using cyclodextrin or its derivatives protects the constituent (i.e., cysteamine compound) from loss of evaporation, from attack by oxygen, acids, visible and ultraviolet light and from intra- and intermolecular reactions.

The general chemical formula of cyclodextrin is $(C_6O_5H_9)_n$. The content of inclusion compound host materials in compositions of the subject invention can range from about 1 to 80 wt %. Preferably, the content of inclusion compound host materials in compositions of the invention range from about 1 to 60 wt %. The actual amount of the inclusion compound host materials used will depend largely upon the actual content of cysteamine compound and additional therapeutic agent(s) used in preparing compositions of the invention.

To provide for the administration of such dosages for the desired therapeutic treatment, compositions of the invention will typically comprise between about 1% and 99%, of at least one cysteamine compound, with at least one additional therapeutic agent and a carrier and/or diluent making up the remainder of the total composition. The dosage used can be varied based upon the age, weight, health, or the gender of the individual to be treated.

Concurrent administration of a cysteamine compound and at least one additional therapeutic agent, in accordance with the subject invention, to a patient diagnosed with insulin resistance preferably enables blood sugar levels to be maintained within normal, acceptable ranges (90-130 mg/dL after fasting—as accepted by the American Diabetes Association).

With certain embodiments, when the additional therapeutic agent is insulin, the preferred daily dosage amount for compositions comprising a cysteamine compound and insulin is about 0.1 to 400 mg/kg of body weight (BW) of cysteamine (or equivalent molar quantity of a cysteamine compound) and about 0.1 to 50.0 units/kg BW of insulin. Preferably, a daily dosage of about 30 mg/kg of BW of cysteamine (or equivalent molar quantity of a cysteamine compound) is concurrently administered with insulin to a patient.

When the additional therapeutic agent is a sulfonylureas (i.e., amaryl, glynase, micronase, glucotrol XL, glucotrol, diabinese, orinase, or tolinase), the preferred daily dosage amount for compositions comprising both a cysteamine compound and a sulfonylureas is about 0.1 to 400 mg/kg or 600 mg/kg BW of cysteamine (or equivalent molar quantity of a cysteamine compound) and about 0.1 to 3,000 mg of a sulfonylureas. Preferably, a daily dosage of about 30 mg/kg of BW of cysteamine (or equivalent molar quantity of a cysteamine compound) is concurrently administered with a sulfonylureas to a patient.

Where a biguanide (i.e., Metformin) is administered concurrently with a cysteamine compound, the preferred dosage amount for each agent is about 0.1 to 400 mg/kg BW of cysteamine (or equivalent molar quantity of a cysteamine compound) and about 0.1 to 3,000 mg of a biguanide. Preferably, a daily dosage of about 30 mg/kg of BW of cysteamine (or equivalent molar quantity of a cysteamine compound) is concurrently administered with a biguanide to a patient.

With embodiments in which at least one α-glucosidase inhibitor (i.e., acarbose, miglitol) is administered concurrently with a cysteamine compound, the preferred daily dosage amount for each agent is about 0.1 to 400 mg/kg BW of cysteamine (or equivalent molar quantity of a cysteamine compound) and about 10 to 1,000 mg of an α-glucosidase inhibitor. Preferably, a daily dosage of about 30 mg/kg of BW of cysteamine (or equivalent molar quantity of a cysteamine compound) is concurrently administered with α-glucosidase inhibitors to a patient.

With embodiments in which thiazolidinediones (i.e., rosiglitazone, pioglitazone) are administered concurrently with a cysteamine compound, the preferred daily dosage amount for each agent is about 0.1 to 400 mg/kg BW of cysteamine (or equivalent molar quantity of a cysteamine compound) and about 0.1 to 200 mg of a thiazolidinedione. Preferably, a daily dosage of about 30 mg/kg of BW of cysteamine (or equivalent molar quantity of a cysteamine compound) is concurrently administered with thiazolidinediones to a patient.

Where a meglitinide (i.e., repaglinide) is administered concurrently with a cysteamine compound, the preferred dosage amount for each agent is about 0.1 to 400 mg/kg BW of cysteamine (or equivalent molar quantity of a cysteamine compound) and about 0.1 to 100 mg of a meglitinide. Preferably, a daily dosage of about 30 mg/kg of BW of cysteamine (or equivalent molar quantity of a cysteamine compound) is concurrently administered with meglitinide to a patient.

With those embodiments in which the additional therapeutic agent is a D-phenylalanine (i.e., nateglinide), the preferred dosage amount for compositions comprising a cysteamine compound and D-phenylalanine is about 0.1 to 400 mg/kg BW of cysteamine (or equivalent molar quantity of a cysteamine compound) and about 10 to 1,000 mg of a D-phenylalanine. Preferably, a daily dosage of about 30 mg/kg of BW of cysteamine (or equivalent molar quantity of a cysteamine compound) is concurrently administered with D-phyenylalanine to a patient.

More preferably, the daily dosage of cysteamine administered to a patient to elicit a desired response is less than about 30 mg/kg BW or less (or equivalent molar quantity of a cysteamine compound) when administered concurrently with a daily dosage of Metfomin at less than about 40 mg/kg of body weight daily, preferably less than 2,000 mg of Metformin daily. The desired response can include (1) a reduction in the severity, duration, or intensity of complications related to a diabetes; (2) regulation in metabolic response to glucose; (3) elimination of complications associated with diabetes; (4) cure and/or ameliorization of diabetes or diabetes associated symptoms; and (5) prevent the onset of diabetes and/or diabetes-related complications, symptoms, or conditions in either a symptomatic or asymptomatic patient.

Following are examples that illustrate procedures for practicing the invention. These examples should not be construed as limiting. All percentages are by weight and all solvent mixture proportions are by volume unless otherwise noted.

EXAMPLE 1

Nineteen male Goto-Kakizaki Wistar rats (GK rats) with weights of 300±20 g were kept in steel cages, 3-4 rats per cage. The cages were changed every two days. Indoor temperature and relative humidity was kept at 23±3° C. and 65±1% respectively. Feed and drinking water was provided. GK rats were permitted a one-month period for adaptation. When the GK rats all demonstrated symptoms of diabetes (i.e., frequent eating, frequent drinking, frequent urination, and high plasma glucose and insulin resistance), they were randomly divided into 3 groups: 7 rats in a control group; 6 rats each in treatment I and II groups.

Prephase Period:

One day prior to experimentation, at 17:00, all of the feed was removed from all groups, but not the drinking water. On the second day, at 09:30, starving plasma glucose was measured for all GK rats. At 10:00, glucose tolerance test (2 g/kg BW) was performed and the plasma glucose level was measured as well for all GK rats. On the third day, the GK rats of the control group were orally administered a saline solution (2 ml/rat) and the GK rats in treatment I and II groups were orally administered a solution of Metformin (17 mg/kg body weight (BW), 2 ml once pre day at 09:30). This regimen was performed for the following several days. On the ninth day, starving plasma glucose was measured and oral glucose tolerance test was performed again for all GK rats in all groups.

Mid-Phase Period:

On the tenth day, the regimen for the GK rats in the treatment II group was changed to an oral administration of Metformin with cysteamine hydrochloride (Metformin 17 mg/kg BW, cysteamine hydrochloride 15 mg/kg BW) for the following 6 days, while the regimen for the control group and the treatment I group remained unchanged. This regimen was performed for six days.

Late-Phase Period:

Six days following the change in regimen, starving plasma glucose was measured and glucose tolerance tests were performed, and blood and tissue samples were collected (liver, duodenum, pancreas gland, fat, and muscle) for all GK rats in all groups. Blood samples were stored at 4° C. for three hours and centrifuged for ten minutes at 3500 rpm. Then, the serum was collected and stored at −20° C. Tissue samples were placed in liquid nitrogen once collected and then stored in −80° C.

The glucose tolerance tests that were performed included the steps of starving the GK rats overnight. Next day at 09:30, starving plasma glucose was measured. At 10:00, oral administration of a glucose solution (2 g/kg BW) was performed. Blood samples were collected via tail vein at 0, 0.5, 1, 2, and 3 hours and then performed with the plasma glucose testing equipment.

The serology testing methods included the steps of measuring serum insulin levels by radioactive measurement; and measuring cholesterol, free fatty acid, and triglyceride using known testing kits and protocol.

Figure 3:
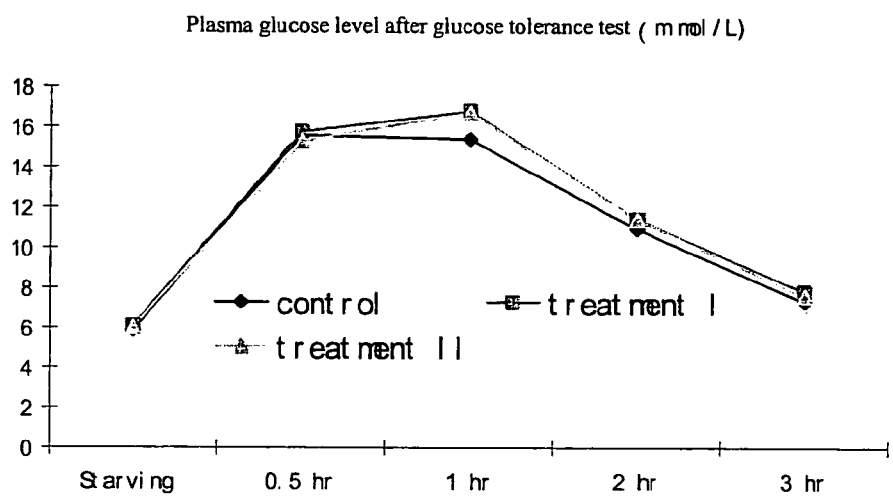
FIGS. 3-5 show results for oral glucose tolerant tests performed on a murine model demonstrating the effectiveness of the systems and methods of the invention.
Figure 4:
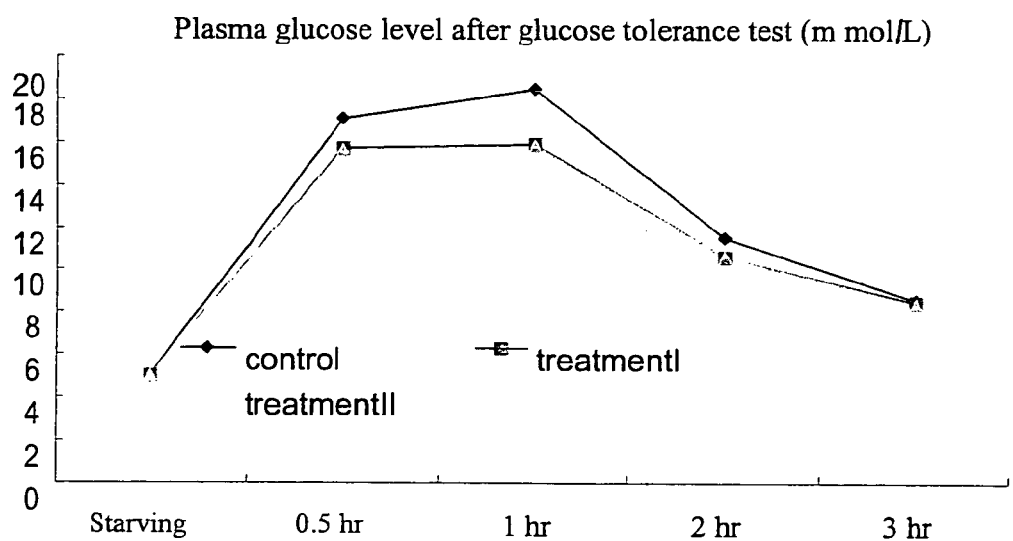
Figure 5:
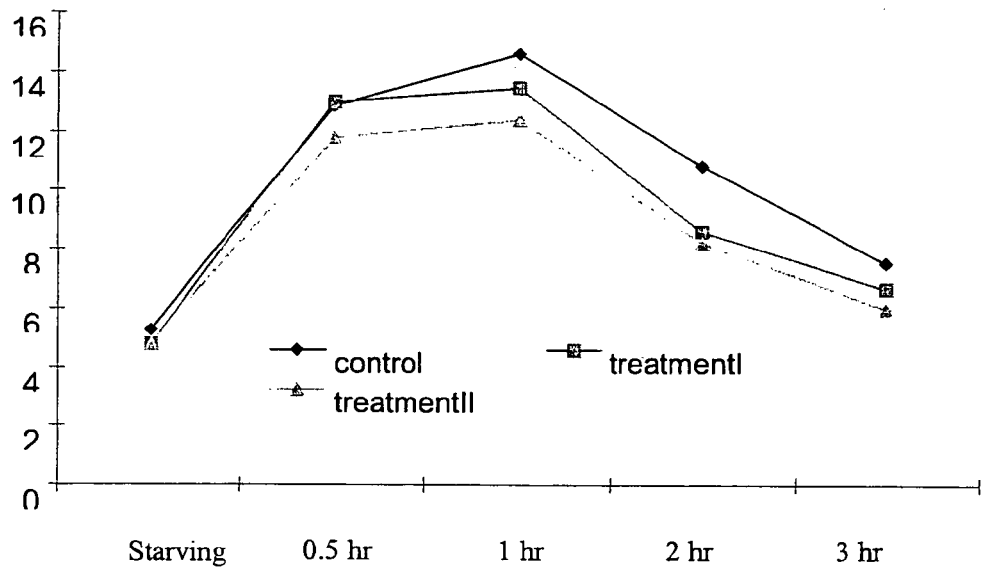
Figure 6:
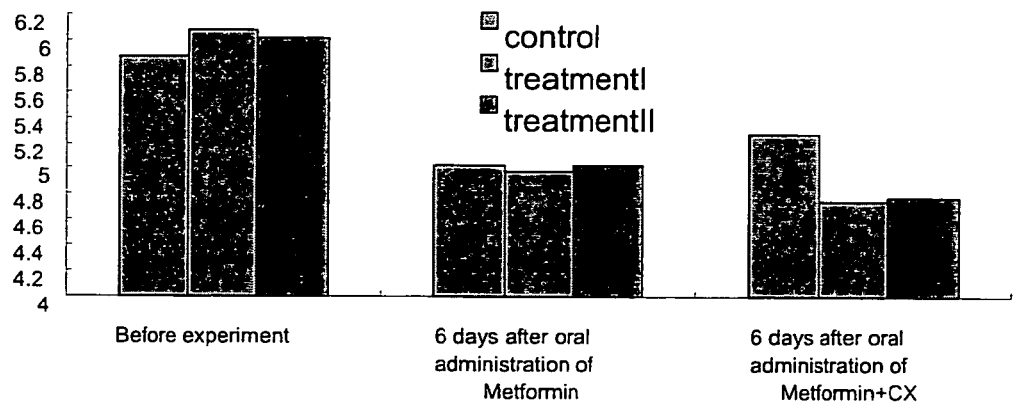
FIG. 6 shows the results of starving plasma glucose tests performed on a murine model demonstrating the effectiveness of the systems and methods of the subject invention.
Figure 7:
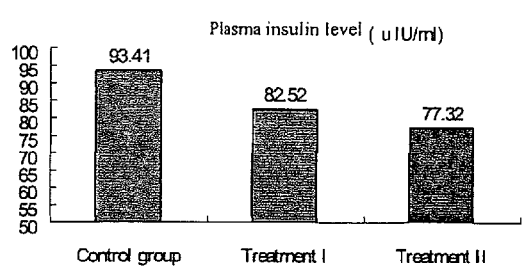
FIGS. 7-10 show results from serology tests performed on a murine model demonstrating the effectiveness of the systems and methods of the subject invention.
Figure 8:
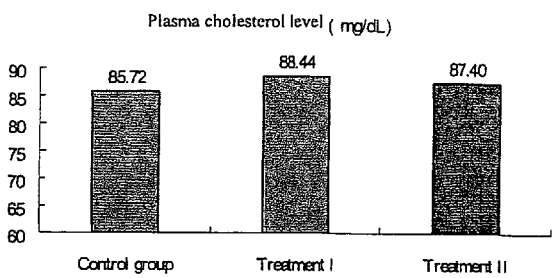
Figure 9:
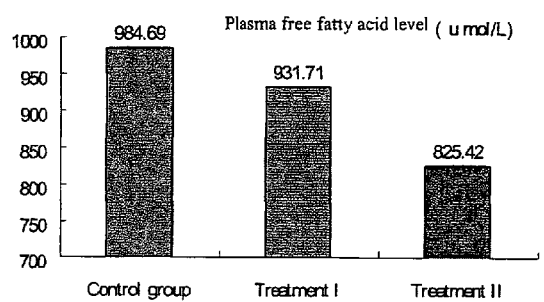
Figure 10:
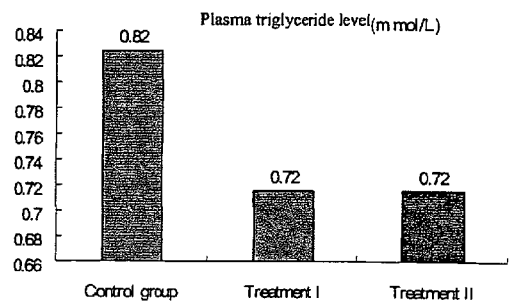

Oral glucose tolerant test results for GK rats in all groups during the pre-phase, mid-phase, and late-phase of the Example are shown in Tables 1, 2 and 3, and FIGS. 3, 4, and 5, respectively. Changes in starving plasma glucose levels during those periods are shown in the tables and summarized in FIG. 6. These results illustrate that the oral administration of Metformin alone, to some extent, lowers duodenal plasma glucose levels and insulin resistance. However, when Metformin is administered concurrently with cysteamine hydrochloride, unexpected, improved results were observed. Specifically, when both Metformin and cysteamine hydrochloride are administered, plasma insulin and free fatty acid levels (indicative of diabetes) were lower than if Metformin (or a cysteamine compound) was administered alone (see FIGS. 7-10). Further, it is expected that lower levels of plasma insulin and free fatty acids would be maintained for a longer period of time after cessation of Metformin/cysteamine hydrochloride administration than if either Metformin or a cysteamine compound were administered alone.

TABLE 1

Glucose tolerance test performed during Pre-Phase

|  | Starving | 0.5 hourr | 1 hour | 2 hours | 3 hours |
| --- | --- | --- | --- | --- | --- |
| Control Group | 5.87 | 15.57 | 15.37 | 10.91 | 7.31 |
| Treatment I | 6.08 | 15.74 | 16.76 | 11.4 | 7.82 |
| Treatment II | 6.02 | 15.28 | 16.7 | 11.38 | 7.6 |

TABLE 2

Glucose tolerance test performed during mid-phase
(6 days after oral administration of Metformin)

|  | Starving | 0.5 hour | 1 hour | 2 hours | 3 hours |
| --- | --- | --- | --- | --- | --- |
| Control Group | 5.03 | 17.04 | 18.46 | 11.5 | 8.59 |
| Treatment I | 4.98 | 15.68 | 15.93 | 10.55 | 8.5 |
| Treatment II | 5.03 | 15.65 | 15.8 | 10.55 | 8.37 |

TABLE 3

Glucose tolerance test performed during late-phase (6 days after oral administration of Metformin + cysteamine hydrochloride)

|  | Starving | 0.5 hour | 1 hour | 2 hours | 3 hours |
|---|---|---|---|---|---|
| Control Group | 5.27 | 12.83 | 14.57 | 10.81 | 7.52 |
| Treatment I | 4.75 | 12.98 | 13.42 | 8.6 | 6.67 |
| Treatment II | 4.77 | 11.75 | 12.37 | 8.17 | 6 |

EXAMPLE 2

Effect of Concurrent Administration of Metformin (at a Higher Dose than that of Example 1) and a Cysteamine Compound on Glucose Metabolism, Glucose Transporter Expression, and Adiponectin Levels in Diabetic Rats Thirty-six Goto-Kakizaki Wistar (GK) rats (purchased from Shanghai Slaccas Laboratory Animal Center) aged about 13 weeks and weighing 321-323 g were acclimated to the animal facility for two weeks in individual cages. Food and water were provided ad libitum.

The 36 GK rats were divided into 4 groups based on body weight (BW) and plasma glucose level. Group 1 (control, n=10) was treated with saline by gavage (2 ml/rat); Group 2 (DC, n=6) was treated with cysteamine hydrochloride by gavage (22.5 mg/kg BW in 2 ml tap water); Group 3 (Metformin, Met, n=10) was treated with Metformin by gavage (34 mg/kg BW in 2 ml tap water); Group 4 (Met+DC, n=10) was treated with Metformin 34 mg/kg BW/day in 2 ml tap water for the first 10 days and then was treated with both cysteamine hydrochloride 22.5 mg/kg BW plus Metformin 34 mg/kg BW in 2 ml tap water for the second 10 days. All animals were treated at 10:00 for 20 days.

The four groups of animals were kept in the same room (temp 23±3° C., relative humidity 65±1%) in different cages with wire mesh bottoms to reduce coprophagia throughout the experiment. The rats were subjected to fasting overnight from 10:00 pm to 09:30 of the following day before being subjected to a glucose tolerance test. The rats were treated with glucose 2 g/kg BW in 2 ml tap water at 09:30 for the glucose tolerance test and the blood was collected from the tail vein at 0.5, 1, 2, and 3 hours after glucose injection. Plasma glucose concentrations were determined by Glucotrendr2 equipment (Roche Diagnostics, Basel, Switzerland). Plasma insulin concentrations were determined by radioimmunoassay (Insulin RIA Kit, NO:0410, purchased from Shanghai Radioimmunoassay Research Institution). The effects on plasma glucose level are shown in Table 4, the effects on plasma insulin and adiponectin levels are shown in Table 5, and the effects on different tissues are shown in Table 6. The "p" value is the comparison with the control group.

With the group that was administered Metformin, the results obtained at 1 hour, 2 hours, and 3 hours are statistically different (p<0.05, denoted as * in Table 4) from the control group. Where cysteamine hydrochloride was administered concurrently with Metformin, the results obtained at 1 hour, 2 hours, and 3 hours are statistically different (p<0.05, denoted as * in Table 4) from the group that was administered only Metformin. The results obtained at 0.5 hour for the concurrent administration of Metformin and cysteamine hydrochloride are decreased as compared to the control group (p=0.059, denoted as + in Table 4).

TABLE 5

Effects of cysteamine hydrochloride (DC) and/or Metformin on Insulin (IU/L) and adiponectin (ng/ml) in GK diabetic rats (Mean ± STD, mmol/L)

| Mean ± STD | Control | CYS | Metformin | Metformin + DC |
|---|---|---|---|---|
| Fasting Insulin | 20.69 ± 1.67 | 22.46 ± 2.65 | 18.75 ± 3.98 | 21.08 ± 4.37 |
| P |  | 0.132 | 0.23 | 0.82 |
| Adiponectin | 3922 ± 528 | 4318 ± 590 | 3917 ± 416 | 3743 ± 366 |
| P |  | 0.034 | 0.971 | 0.206 |

The results from Table 5 regarding the glucose levels of the group that was administered Metformin alone at the 1 hour, 2 hour, and 3 hour time points following glucose intake were statistically significantly different from respective control groups.

Cysteamine hydrochloride alone did not affect either glucose levels or insulin levels in GK diabetic rats. Administration of Metformin resulted in a decreased, but not statistically significant, insulin level. However, when Metformin was administered concurrently with cysteamine hydrochloride, an improvement in lowering glucose levels (especially when compared against the therapeutic effect of Metformin when administered alone) was observed at all time points except at the Fasting time point. It was also observed that adiponectin was significantly increased by cysteamine but not Metformin alone.

TABLE 6

Effects of cysteamine hydrochloride (DC) and/or Metformin or in combination on glucose transporter (glut4) expression in different tissues of GK diabetic rats (Mean ± STD), expressed as fold changes compared with control level

|  | DC | Metformin | Metformin + DC |
|---|---|---|---|
| liver | 3.77 ± 3.15 | 2.43 ± 1.85 | 2.8 ± 1.0 |
| p | 0.002 | 0.31 | 0.04 |
| muscle | 1.5 ± 0.74 | 1.38 ± 0.67 | 1.31 ± 0.75 |
| p | 0.001 | 0.152 | 0.633 |
| adipocyte | 2.7 ± 1.16 | 2.14 ± 1.39 | 3.49 ± 2.37 |
| p | 0.005 | 0.095 | 0.095 |

TABLE 4

Glucose tolerance test for cysteamine hydrochloride (DC) and/or Metformin in GK diabetic rats (Mean ± STD, mmol/L)

|  | N | Fasting | 0.5 hour | 1 hour | 2 hours | 3 hours |
|---|---|---|---|---|---|---|
| Control | 10 | 5.56 ± 0.22 | 15.78 ± 1.96 | 15.32 ± 1.58 | 11.52 ± 1.45 | 8.85 ± 0.8 |
| DC | 6 | 5.80 ± 0.36 | 16.68 ± 1.1 | 15.68 ± 0.8 | 11.00 ± 0.8 | 8.33 ± 0.64 |
| Metformin | 10 | 5.53 ± 0.53 | 15.24 ± 1.34 | 13.98 ± 0.95* | 9.62 ± 0.83* | 7.71 ± 1.37* |
| Metformin + DC | 10 | 5.46 ± 0.46 | 14.07 ± 1.84+ | 12.44 ± 0.96* | 7.71 ± 0.83* | 6.35 ± 0.73* |

As shown in Table 6, a cysteamine compound (such as cysteamine hydrochloride) can significantly increase the expression of total glut4 in liver, muscles, adipocytes in the GK rats. This increase is much greater in liver and adipocytes as compared to muscles. Metformin alone also increased, but not significantly, the expression levels of total glut4 in all tissues measured. However, the levels of total glucose transporter (glut4) expression were further enhanced when Metformin was concurrently administered with a cysteamine compound.

EXAMPLE 3

Effect of Administration of a Cysteamine Compound on Diabetic Rats

A small open-label, randomized trial was carried out at the national reference center for diabetes in China. Sixty patients of both sexes (ages ranged from 30 to 75 years old) diagnosed with diabetes type II were recruited. All subjects were informed and gave their consent to participate. Diabetes was diagnosed based on the WHO criteria set in 1999. In addition, patients selected fulfilled the following criteria: (1) a diabetes history of less than 5 years; (2) fasting plasma glucose level between 7-14 mmol/L; (3) serum triglyceride level of 2.5 mmol/L or higher; (4) urine protein excretion of 30 mg/day or higher; and (5) no intake of anti-lipid drugs and ACE inhibitors in the past one month.

Patients with the following conditions were excluded from the study: (1) dysfunction of heart, liver and/or kidney; (2) with acute diabetic complications and/or any acute cardiovascular complications or other chronic diseases in the past three months; and (3) pregnancy or nursing.

Patients were divided randomly into four groups of 15 patients each. A control group of subjects was not administered anti-diabetic drugs. The cysteamine alone (DC) group was treated with 540 mg/day of cysteamine hydrochloride. In the Metformin alone (Met) group, the dose of Metformin remained unchanged during the two months period. For the DC+Met group, patients remained on the same dose of Metformin they were originally administered, including an additional 100 mg/day of cysteamine hydrochloride. All patients were subjected to treatments for two months and samples were collected and measured at the beginning of, one month after, and two month after the trial for analysis.

suggest that a cysteamine compound can be administered to a patient to improve insulin resistance. Further, the results indicate that administration of cysteamine hydrochloride decreases significantly insulin-like growth factor 1 (IGF1), C peptide (CP), and microalbuminuria (obvious but not statistically significantly) in a patient, which suggests that a cysteamine compound can be used either alone or in combination with additional therapeutic agents to treat or prevent complications associated with diabetes and insulin resistance syndrome. The abbreviation FBS stands for fasting blood sugar.

EXAMPLE 4

Formulations

The novel compositions of the invention comprise 1 to 95 wt % of a cysteamine compound and 1 to 80 wt % of a carrier such as inclusion compound host materials. In certain embodiments, the compositions of the invention further comprise an additional therapeutic agent of a dosage to ensure therapeutic results when concurrently administered with a cysteamine compound.

In this example, the inclusion compound host materials comprise mainly cyclodextrin and/or its derivative which are selected from a group included methyl β-cycoldextrin (M-β-CD), hydropropyl β-cycoldextrin (HP-β-CD), hydroethyl β-cycoldextrin (HE-β-CD), polycyclodextrin, ethyl β-cyclodextrin (E-β-CD) and branched cycoldextrin. While the workable content of the inclusion compound host materials in the cysteamine-containing composition ranges from 1 to 80 wt %, a preferable workable range of 1 to 60 wt % and a more preferable workable range of 10 to 40 wt % of the inclusion compound host materials may be also be used. The actual amount of the inclusion compound host materials used will depend on the actual content of the cysteamine compound and additional therapeutic agent(s) used in preparing the cysteamine-containing composition.

In certain embodiments, the compositions made according to the present invention are in the form of small granules, each of which has a preferable diameter of substantially 0.28 to 0.90 mm. These granules are prepared using a microencapsulation method. The method involves using a macromolecular substance having inclusion property. One substance that may be used is the inclusion compound host materials (which comprises mainly cyclodextrin) described above. The inclu-

TABLE 7

Effects of cysteamine hydrochloride on lipid and insulin in diabetic patients

|  | Pre-treatment | n | Post-treatment | n | Paired Difference | 95% CI | p |
|---|---|---|---|---|---|---|---|
| IGF | 49.36 ± 5.75 | 10 | 44.37 ± 7.28 | 10 | 4.99 ± 5.12 | 1.33~8.65 | 0.013 |
| FINS | 35.39 ± 14.43 | 6 | 13.25 ± 6.36 | 6 | 22.14 ± 19.39 | 1.79~42.5 | 0.038 |
| FCP | 739 ± 183 | 7 | 557 ± 119 | 7 | 182 ± 164 | 30.1~333.9 | 0.026 |
| FBS | 7.52 ± 1.57 | 11 | 8.21 ± 2.43 | 11 | −0.69 ± 2.11 | −2.11~0.72 | 0.301 |
| HOMA | 11.94 ± 4.62 | 6 | 5.43 ± 3.19 | 6 | 6.51 ± 4.94 | 1.32~11.7 | 0.023 |
| UA | 389 ± 50.98 | 11 | 359 ± 60.16 | 11 | 29.5 ± 37.87 | 4.07~54.95 | 0.027 |
| 24 h Microalbuminuria | 42.73 ± 31.33 | 8 | 30.97 ± 25.12 | 8 | 11.77 ± 40.73 | −22.28~45.82 | 0.441 |

As shown in Table 7, the administration of cysteamine hydrochloride decreases significantly fasting insulin (FINS), HOMA (Homeostasis Model Assessment), and blood uric acid (UA) levels. In contrast, when Metformin was administered alone, there was only a decrease in IGF-1. Such results sion compound host materials are a macromolecular substance which acts as a molecular capsule to engulf the molecules of cysteamine and/or additional therapeutic agent(s), whereby the cysteamine compound and/or the therapeutic in the composition are protected and insulated from light, heat, air and moisture of the surroundings. The stability of the cysteamine compound is thus preserved. The inclusion compound host materials used in the micro-encapsulation method are preferably a cyclic polysaccharide compound having 6 to 12 glucose molecules, which is produced by reacting cyclodextrin glycosidtransferase and starch in the presence of Bacillus. Various studies using acute, subacute and chronic toxic tests have shown that the macromolecular substance can reduce toxic levels in a patient. Subsequent to the microencapsulation process, each granule may be coated with at least one and preferably a plurality of layers of the coating materials described above.

The following is an example of how to prepare formulations described above for a cysteamine compound. In a jacketed reactor linked with polytetrafluoroethylene and equipped with a polytetrafluoroethylene coated stirrer, 4080 g of 75 wt % cysteamine hydrochloride solution in ethanol is added with mainly nitrogen being the atmosphere. The purity, melting point and burning residue of the cysteamine used are preferably 98% or above, 66 to 70° C. and 0.05% or below respectively. 1200 g β-cyclodextrin is then added into the reactor similarly under the protection of nitrogen gas. (The quality of β-cyclodextrin is in accordance with the requirements for a food additive. In particular, the dry basis purity is more than 98%; the weight loss by drying is less than 10.0%; the burning residue is less than 0.2%; the content of heavy metal is less than 10 ppm; the arsenic content is less than 2 ppm.) The mixture is then heated for 3 hours at 40° C. Heating is then stopped and stirring continues for two hours thereafter, products resulted therefrom are then grounded and sieved through a screen (e.g., 40-mesh) filter after the products have been vacuum dried at a temperature of 40-50° C. All parts of the equipment, which may come in contact with the ingredients of the composition, should preferably be made of stainless steel.

In a tank-type mixer, 4200 g (on dry basis) of the cysteamine compound, which has undergone the inclusion process as described, 2600 g of the fillers, and 1200 g of the disintegrants and 1700 g binders are added under the protection of a dry surroundings. These ingredients are then thoroughly mixed, and a suitable amount of anhydrous ethanol may be added and then mixed therewith. The resulting mixture presents a soft material with moderate hardness, so that it can be shaped into a ball by a light hold of palms. The ball-shaped resulting mixture may then be broken up by a light touch. After the mixture is pelleted by a granulator under the protection of nitrogen, the small granules resulting therefrom is immediately introduced to a fluid-bed dryer, and is then dried at the temperature of 40-50° C. in a substantially vacuum environment.

Enteric coating materials are then prepared by a method with the following formulation: cellulose acetate phthalate 8.0 g, polyethylene glycol terephthalate 2.4 ml, ethyl acetate 33.0 ml and isopropyl acetate 33.6 ml. The resultant granules obtained above are uniformly coated under the protection of nitrogen with at least one layer but preferably a plurality of layers the enteric coating materials described above. The enteric coating materials are dissolvable only at an alkaline environment. This can prevent the cysteamine compound from prematurely escaped from the composition while it is still in the stomach of the patient. As noted earlier, a cysteamine compound can adversely stimulate gastric mucous of the stomach of a patient.

The resultant granules of the cysteamine-containing composition are then dried completely in a substantially vacuum dryer at a temperature of 40 to 50° C. Then, all solvents are removed. The resultant granules are then allowed to cool to room temperature, the micro-capsula were mixed with a suitable amount of flavoring and smelling agents by a cantilever double helix blender. The cysteamine-containing composition is a microcapsule with its interior having cysteamine hydrochloride and cyclodextrin, and with its exterior coated with the enteric coating materials.

The composition produced will exhibit small granular (or micro-particulate) shape having smooth surface, good flow property, and is easy to be blended with various animal feeds. The diameter of each granule of the composition is preferably 0.28 to 0.90 mm. The composition also has excellent stability. It has been found that after the composition is packaged with sealed plastic bags and stored for one year in a cool, dark and dry place, their properties remain unchanged.

The composition having the particular construction described above has a number of functional advantages over a cysteamine compound by itself. Firstly, the activity of the cysteamine compound and/or additional therapeutic agent(s) contained in the composition is preserved after it has been produced. Secondly, the composition should not cause any noticeable gastro side effects to the patient. Thirdly, the activity of the composition is preserved not only during storage but more importantly when traveling through the gastro-tract until it reaches the intestines of the patient.

All patents, patent applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and preview of this application.

We claim:

1. A method for treating type II diabetes wherein said method comprises concurrently administering to a patient an effective amount of cysteamine, or a salt thereof, with at least one additional therapeutic agent which is Metformin or insulin, and wherein the effective amount of the cysteamine administered to the patient is less than about 400 mg/kg of body weight.

2. The method, according to claim 1, wherein the effective amount of the cysteamine, or its salt, administered to the patient is about 30 mg/kg of body weight or an equivalent molar quantity.

3. The method, according to claim 1, wherein said cysteamine salt is cysteamine hydrochloride or cysteamine phosphate.

4. The method, according to claim 1, wherein said cysteamine and additional therapeutic agent are taken orally, parenterally, intravenously, intramuscularly, transdermally, via buccal route, subcutaneously, or via suppository.

5. The method, according to claim 1, wherein the effective amount of the Metformin is less than about 40 mg/kg of body weight per day.

* * * * *

UNITED STATES PATENT AND TRADEMARK OFFICE
CERTIFICATE OF CORRECTION

| | | |
|---|---|---|
| PATENT NO. | : 7,442,720 B2 | Page 1 of 1 |
| APPLICATION NO. | : 11/017164 | |
| DATED | : December 28, 2004 | |
| INVENTOR(S) | : Chan et al. | |

It is certified that error appears in the above-identified patent and that said Letters Patent is hereby corrected as shown below:

Title Page, item [57]
Abstract,
Line 3 "compositions methods for treating" should read --compositions and methods for treating--.

Signed and Sealed this

Second Day of June, 2009

JOHN DOLL
*Acting Director of the United States Patent and Trademark Office*

UNITED STATES PATENT AND TRADEMARK OFFICE
CERTIFICATE OF CORRECTION

PATENT NO.         : 7,442,720 B2
APPLICATION NO. : 11/017164
DATED              : October 28, 2008
INVENTOR(S)        : Chan et al.

Page 1 of 1

It is certified that error appears in the above-identified patent and that said Letters Patent is hereby corrected as shown below:

Title Page, item [57]
Abstract,
Line 3 "compositions methods for treating" should read --compositions and methods for treating--.

This certificate supersedes the Certificate of Correction issued June 2, 2009.

Signed and Sealed this

Twenty-third Day of June, 2009

JOHN DOLL
*Acting Director of the United States Patent and Trademark Office*